(12) United States Patent
Pisano et al.

(10) Patent No.: US 9,023,861 B2
(45) Date of Patent: May 5, 2015

(54) ANTICANCER COMBINATION OF ARTEMISININ-BASED DRUGS AND OTHER CHEMOTHERAPEUTIC AGENTS

(75) Inventors: Claudio Pisano, Aprilia (IT); Loredana Vesci, Rome (IT)

(73) Assignee: Sigma-Tau Industrie Farmaceutiche Riunite, S.p.A., Rome (IT)

( * ) Notice: Subject to any disclaimer, the term of this patent is extended or adjusted under 35 U.S.C. 154(b) by 0 days.

(21) Appl. No.: 13/518,185

(22) PCT Filed: Dec. 6, 2010

(86) PCT No.: PCT/EP2010/068924
§ 371 (c)(1),
(2), (4) Date: Jun. 21, 2012

(87) PCT Pub. No.: WO2011/076547
PCT Pub. Date: Jun. 30, 2011

(65) Prior Publication Data
US 2012/0258181 A1     Oct. 11, 2012

(30) Foreign Application Priority Data

Dec. 23, 2009   (EP) .................................... 09180666

(51) Int. Cl.
*A61K 31/24*     (2006.01)
*A61K 31/335*    (2006.01)
*A61K 31/4745*   (2006.01)
*A61K 31/704*    (2006.01)

(52) U.S. Cl.
CPC .............. *A61K 31/24* (2013.01); *A61K 31/335* (2013.01); *A61K 31/4745* (2013.01); *A61K 31/704* (2013.01)

(58) Field of Classification Search
CPC . A61K 2300/00; A61K 31/24; A61K 31/335; A61K 31/4745; A61K 31/704
See application file for complete search history.

(56) References Cited

U.S. PATENT DOCUMENTS

| | | |
|---|---|---|
| 5,578,637 A | 11/1996 | Lai et al. |
| 2008/0108659 A1* | 5/2008 | Gandhi et al. ................ 514/323 |

FOREIGN PATENT DOCUMENTS

| | | |
|---|---|---|
| WO | 02/13826 A1 | 2/2002 |
| WO | 2004/071506 A1 | 8/2004 |
| WO | WO 2009/114459 * | 9/2009 |

OTHER PUBLICATIONS

CN 101856352. Machine Translation. Published Oct. 13, 2010.*
CN 101856352. Derwent Abstract. Published Oct. 13, 2010.*
Donawho et al. ABT-888, an orally active poly(ADP-ribose) polymerase inhibitor that potentiates DNA-damaging agents in preclinical tumor models. Clin. Cancer Res. 2007: 13(9), May 1, 2007.*
Merck Manual: Home Edition. titled: Combination therapy. Chabner et al. Aug. 2007. Electronic Resource: [http//merck.com/mmhe/sec15/ch182/ch182h.html]. Retrieved online on Sep. 11, 2010.*
Shao et al. Effects of dihydroartemisinin on proliferation and apoptosis of colon carcinoma cell line SW480. Wuhan Daxue Xuebao, Yixueban. vol. 29, Issue 3, pp. 319-323, 2008; English abstract only.*
Protein page: PARP1 (human). Electronic Resource. Retrieved on Oct. 9, 2014. Electronic address: [http://www.phosphosite.org/proteinAction.do?id=9166&showAllSites=true].*
Zhan et al. Experimental study on the intervention of dihydroartemisinin on colorectal cancer growth in animal models. Guangzhou Zhongyiyao Daxue Xuebao, vol. 26, Issue 5, pp. 465-467, 2009.*
Jung, M. et al, "Recent Advances in Artemisin and Its Derivatives as Antimalarial and Antitumor Agents," Current Medicinal Chemistry, Journal of Chinese Integrative Medicine, vol. 11, No. 10, pp. 1265-1284 (2004).
Zhang et al, "Artesunate Combined with Vinorelbine Plus Cisplatin in Treatment of Advanced Non-Small Cell Lung Cancer: A Randomized Controlled Trial," Jounral of Chinese Integrative Medicine, vol. 6, No. 2, Feb. 15, 2008, XP002568355. http://www.jcimjournal.com./articles/publishArticles/pdf/200831079205.pdf (abstract).
Chen Weiqiang, et al., Inhibition of Growth on Human Lung . . . , Modern Oncology, vol. 14, No. 3, pp. 284-288, 2006.
Taiwan Office Action for Taiwanese Application No. 099140203 filed on Aug. 14, 2014.
Xiao-Jia Huang, et al., Dihydroartemisinin Potentiates the Cytotoxic . . . , Pharmacology, vol. 82, No. 1, pp. 1-9, 2008.
Tao Chen, et al., Dihydroartemisinin Induces Apoptosis and Sensitizes . . . , J. Cell. Mol. Med., vol. 13, No. 7, pp. 1358-1370, 2009.
Cherrie K. Donawho, et al., ABT-888, An Orally Active Poly(ADP-Ribose) Polymerase Inhibitor . . . , Clin. Cancer Res. vol. 13, No. 9, pp. 2728-2737, 2007.
Japanese Office Action for Japanese Application No. 2012-545201 filed on Jan. 6, 2015.

* cited by examiner

*Primary Examiner* — Anna Pagonakis
(74) *Attorney, Agent, or Firm* — Lucas & Mercanti, LLP

(57) ABSTRACT

The present invention relates to combinations between artemisinin-based potent anti-malarial agents, selected from the group consisting of ART, DHA and ARM, and a further chemotherapeutic drug selected from the group consisting of a camptothecin derivative, or a PARP-1 inhibitor, or an intercalating DNA agent, or an alkylating agent. Such combinations, showed medium to strong synergism in various models of cancer, in particular in NSCL.

6 Claims, No Drawings

ANTICANCER COMBINATION OF ARTEMISININ-BASED DRUGS AND OTHER CHEMOTHERAPEUTIC AGENTS

This application is a U.S. national stage of PCT/EP2010/068924 filed on Dec. 6, 2010 which claims priority to and the benefit of European Application No. EP09180666.1 on Dec. 23, 2009, the contents of which are incorporated herein by reference.

FIELD OF THE INVENTION

The present invention relates to new combinations of artemisinin-based drugs selected from the group consisting of artemisinin, dihydroartemisinin and artemether, together with chemotherapeutic agents, pharmaceutical compositions containing them and their use as cytotoxic compositions.

BACKGROUND OF THE INVENTION

Besides their well known antimalarial activities, artemisinin-based drugs such as artemisinin (ART), dihydroartemisinin (DHA), artemether (ARM), and artesunate (ARS) have been reported recently to be also endowed of cytotoxic properties through induction of apoptosis (Singh N. P., et al., *Anticancer Res.*, 2004, 24, 2277; Nam W., et al., Head Neck, 2007, 29, 335).

Even if DHA possesses some cytotoxic properties, the latter are usually observable at relatively high drug concentration. Over the past few years, ART derivatives have emerged because endowed of more pronounced cytotoxic properties than DHA itself, against a wide range of cancer cells suggesting some potential for the treatment of various cancers such as human hepatocellular carcinoma (Hou J., et al., *Clin. Cancer Res.*, 2008, 14, 17, 5519), leukemia (Lu J. J., et al., *Canc. Biol. Ther.*, 2008, 7, 7, 1017), prostate cancer, non-small cell lung cancer (Lu Y. Y., et al., *J. Biomed. Sci.*, 2009, Feb. 2, 16:16), pancreas (Chen H., et al., Anti-Cancer Drugs, 2009, 20, 2, 131) and cervical cancer (Disbrow G. L., et al., *Cancer Res.*, 2005, 65, 23, 10854).

It has been shown that compositions of some known antimalarial and various chemotherapeutics can lead to improved cytotoxic combinations. For example, ARS and tyrosine kinase inhibitor OSI-774 produce mainly additive effect on glioblastoma multiforme cell lines (Efferth T., et al., *Biochem. Pharmacol.*, 2004, 67, 9, 1689); ARS and the anthracycline intercalating agent doxorubicin showed synergistic activity on leukemic T-cells (Efferth T., et al., *PLoS One*, 2007, 2, 1, e693), the anti-CD20 antibody rituximab potentiates the cytotoxic effect of ARS at high concentrations (Sieber S., et al., *Int. J. Oncol.*, 2009, 35, 1, 149). Lately, a clinical trial aimed at comparing the efficacy of a cocktail containing vinorelbine and cisplatin with that of said cocktail in combination with ARS was reported. The combination treatment did not provide any improvement in the short term survival rate, nor in the mean survival time or in the one year survival rate, thus failing to demonstrate any benefit over the single cocktail regimen on these important end point (Zhang Z. Y., et al., *J. Integrative Med.*, 2008, 6, 2, 134).

WO2004/071506 reported that ART could be used for treating tumours induced by oncogenic viruses and for treating viral infections. The inventors also reported that combinations of ART with further anti-cancer drugs could be used favourably. However, no biological data regarding such combination treatment were reported to support the alleged synergistic activity.

On another side, DHA and gemcitabine showed a modest 1.2 fold increase in inhibition of proliferation of HepG2 and Hep3B hepatoma cells (Hou J., et al., *Clin. Cancer Res.*, 2008, 14, 17, 5519).

Besides those disclosures, some contradictory data also appeared in the literature. Synergistic effects between DHA and the well known HDAC inhibitor sodium butyrate have been reported (Singh N. P., et al., *Anticancer Res.*, 2005, 25, 6B, 4325). It is noteworthy that these experiments were all conducted in the presence of 12 µM of holotransferrin, which, as an iron-carrying protein, acted to enhance iron penetration into the cells. This phenomenon is known to improve DHA reactivity by enhancing radical generation from the peroxy moiety (Disbrow G. L., et al., *Cancer Res.*, 2005, 65, 23, 10854). However, the same authors have also disclosed previously in a patent application (WO199634602) that DHA and holotransferrin alone proved to lead to enhanced cytotoxic activity on MOLT-4 lymphoblastoid cells as well as in a canine mast cells carcinoma. Strangely, if the paper from 2005 highlights the fact that 10 µM DHA in the presence of 12 µM of holotransferrin had no effect on Molt-4 cells (FIG. 1C, page 4327), the same experimental conditions used in the patent application were reported to lead to 75% reduction in cell count at 8 hours. U.S. Pat. No. 5,578,637 also reported combinations involving endoperoxide-containing compounds wherein the presence of an iron enhancing agent was mandatory.

EP1658844 reports the outcome of a treatment therapy of two patients affected by uveal melanoma involving the use of ARS in combination with dacarbazin in the presence or absence of a concomitant iron therapy, the latter was aimed at increasing the efficacy of ARS. Meanwhile the first patient, who did not receive the supplementary iron medication, died 23 months after entry into stage IV according to AJCC (Balch C. M., et al., *J. Clin. Oncol.*, 2001, 19, 16, 3635), the second patient, who received the supplementary iron medication, was still alive at the time this patent application was filed.

WO200213826 disclosed combinations of the anti-malarial agents chloroquine, hydroxychloroquine and primaquine with the anti-cancer agents cisplatin and doxorubicin. Such combinations resulted in a better anti-cancer efficacy on few cell-lines, above all when the anti-malarial drug was used in high concentration. Quinine derivatives, and in particular hydroxychloroquine have recently been reported to block autophagy, the latter being recognized to be a tumour resistance mechanism allowing cancer cells to survive in stress conditions (Rubinsztein D. C., et al., *Nature Rev. Drug Disc.*, 2007, 6, 304). Furthermore, the difference in the mechanism of action of quinine-like drugs and artemisinin-like drugs is reported (Jung M., et al., Curr. Med. Chem., 2004, 11, 10, 1265; Meshinick S. R., et al., *Microbiol. Rev.*, 1996, 60, 301; Wu W. M., et al., *Chem. Soc. Chem. Commun.*, 1996, 2213; Wu W. M., et al., *J. Am. Chem. Soc.*, 1998, 120, 3316). Jung M., et al. cited herein above also reported that novel C-12 non-acetal type deoxyartemisinin were found to possess exceptionally high in vitro antitumour activity. Such derivatives are structurally unrelated to the compounds of the present invention.

Nevertheless, other pharmaceutical combinations involving either ART, DHA or ARM and a second chemotherapeutic agent chosen from the group consisting of a camptothecin derivative, or a PARP-1 inhibitor, or an intercalating DNA agent, or an alkylating agent have never been reported to produce synergistic effects toward the treatment of cancer diseases.

Camptothecin derivatives originated from the discovery more than forty years ago of the alkaloid camptothecin, further referred to as CPT. The latter is reputed to be endowed of potent and wide spectrum anti-cancer activity. A lot of efforts, from numerous medicinal chemistry groups, have been devoted at improving the physico-chemical properties of CPT itself. Potent CPT derivatives can be found for example in EP1044977 (filed in the name of the Applicant). Zunino F., et al. also nicely reviewed the latest advances in the field of CPT derivatives (Zunino F., et al., Curr. Pharm. Des., 2002, 8, 2505).

A promising role of PARP-1 inhibition in oncology was established on the basis that BRCA1 and BCRA2 knock-out cell lines were found to be highly sensitive to PARP-1 inhibitors, the latter provoking cell death. BRCA1 and BCRA2 protein mutations can lead to a major risk of breast, ovary prostate and pancreas cancers (e.g., MK-4827, Jones P., et al., J. Med. Chem., 2009, 52, 22, 7170). WO2006110816 reported PARP inhibitors, among which ABT-888, endowed with anti-inflammatory properties besides possessing anti-proliferative properties.

PARP-1 inhibitors have also been reported to enhance the cytotoxic activities of anti-cancer drugs such as topoisomerase-I inhibitors (Delaney C. A., et al., Clin. Cancer Res., 2000, 6, 2860-2867) and cisplatin (Miknyoczki S. J., et al., Mol. Cancer Ther., 2003, 2, 371). Combination therapy on BRCA2/p53 deficient mice developing mammary tumours involving the use of PARP-1 inhibitor AZD2281 (Menear K. A., et al., J. Med. Chem., 2008, 51, 6581) together with carboplatin was reported lately. Such a study showed no advantage over carboplatin monotherapy. Only the time to tumour relapse was increased when the PARP-1 inhibition was prolonged (Hay T., et al., Cancer Res., 2009, 69, 9, 3850). The patent application WO2008063644 (Cephalon) reports that some carbazole derivatives as PARP-1 inhibitors cause radio-sensitization in human glioblastoma related xenograf model. A clinical trial (NCT00920595) is currently recruiting patient for a study regarding a combination therapy against solid tumours involving a PARP inhibitor and the methylating agent temozolomide.

Intercalating DNA agents such as anthracycline or acridine derivatives have been known and used for years in the treatment of various form of cancers; the best known derivatives being doxorubicin, daunorubicin, and dactinomycin.

Treatment of cancer remains largely unsatisfactory because of drug resistance phenomenon or dose-limiting cytotoxicity. Therefore, new treatments involving potent and safer drugs are highly desired to further increase the chance of finding an adequate therapies against cancer diseases.

DESCRIPTION OF THE INVENTION

Notwithstanding uncertainty about alleged activity of DHA-containing compositions coupled to an unknown mechanism of action, rendering the usefulness of DHA and/or its analogues as cytotoxic agents rather hypothetical, we surprisingly found that artemisinin-based potent anti-malarial agents, selected from the group consisting of ART, DHA and ARM, when combined with a camptothecin derivative, or a PARP-1 inhibitor, or an intercalating DNA agent, or an alkylating agent, provoked medium to strong synergism in various models of cancer, in particular in NSCL.

One embodiment of the present invention relates to a chemotherapeutic combination consisting of: a pharmaceutical agent (a) selected from the group consisting of ART, DHA and ARM; and a chemotherapeutic agent (b) selected from the group consisting of camptothecin derivatives, PARP-1 inhibitors, intercalating DNA agents and alkylating agents; wherein within said combination, each ingredient (a) and (b) are formulated separately from each other or are formulated in a single dosage form.

A further embodiment of the present invention relates to a chemotherapeutic combination consisting of: a pharmaceutical agent (a) selected from the group consisting of ART, DHA and ARM; and a chemotherapeutic agent (b) selected from the group consisting of camptothecin derivatives, PARP-1 inhibitors, intercalating DNA agents and alkylating agents; wherein within said combination, pharmaceutical agent (a) and chemotherapeutic agent (b) are formulated in a single dosage form suitable for concomitant use of both agents.

A still further embodiment of the present invention relates to a chemotherapeutic combination consisting of: a pharmaceutical agent (a) selected from the group consisting of ART, DHA and ARM; and a chemotherapeutic agent (b) selected from the group consisting of camptothecin derivatives, PARP-1 inhibitors, intercalating DNA agents and alkylating agents; wherein within said combination, pharmaceutical agent (a) and chemotherapeutic agent (b) are formulated separately, which is suitable for separate, concomitant or sequential use.

In a preferred embodiment, within said combination the pharmaceutical agent (a) is DHA.

In a further preferred embodiment, within said combination the chemotherapeutic agent (b) is a camptothecin derivative.

In a more preferred embodiment, the camptothecin derivative is one of those disclosed in U.S. Pat. No. 6,242,457 or is irinotecan or its active metabolite SN-38. Preferred camptothecin derivatives are selected from the group consisting of 7-methoxyiminomethylcamptothecin, 7-methoxyiminomethyl-10-hydroxycamptothecin, 7-(ter-butoxycarbonyl-2-propoxy)-iminomethylcamptothecin, 7-ethoxyiminomethyl-camptothecin, 7-isopropoxy-iminomethylcamptothecin, 7-(2-methylbutoxy)-iminomethylcamptothecin, 7-t-butoxy-iminomethylcamptothecin, 7-t-butoxyiminomethyl-10-hydroxycamptothecin, 7-t-butoxyiminomethyl-10-methoxy-camptothecin, 7-(4-hydroxybutoxy)-iminomethylcamptothecin, 7-triphenyl-methoxyiminomethylcamptothecin, 7-carboxymethoxyiminomethylcamptothecin, 7-(2-amino)-ethoxyiminomethyl-camptothecin, 7-(2-N,N-dimethylamino)-ethoxyiminomethylcamptothecin, 7-allyloxyiminomethylcamptothecin, 7-cyclohexyloxyiminomethylcamptothecin, 7-cyclohexyl-methoxyiminomethylcamptothecin, 7-cyclooctyloxyiminomethylcamptothecin, 7-cyclooctylmethoxyiminomethyl-camptothecin, 7-benzyloxy-iminomethylcamptothecin, 7-[(1-benzyloxyimino)-2-phenylethyl]camptothecin, 7-(1-benzyloxyimino)-ethylcamptothecin, 7-phenoxy-iminomethylcamptothecin, 7-(1-t-butoxyimino)-ethylcamptothecin, 7-p-nitrobenzyloxyiminomethylcamptothecin, 7-p-methyl-benzyloxyiminomethylcamptothecin, 7-pentafluorobenzyloxyiminomethyl-camptothecin, 7-p-phenylbenzyloxyimino-methyl-camptothecin, 7-[2-(2,4-difluorophenyl)-ethoxy] iminomethylcamptothecin, 7-(4-t-butylbenzyloxy)-iminomethylcamptothecin, 7-(1-adamantyloxy)-iminomethyl-camptothecin, 7-(1-adamantylmethoxy)-iminomethylcamptothecin, 7-(2-naphthyloxy)-iminomethyl-camptothecin, 7-(9-anthrylmethoxy)-iminomethyl-camptothecin, 7-oxiranylmethoxyiminomethyl-camptothecin, 7-(6-uracyl)-methoxy-iminomethylcamptothecin, 7-[2-(1-uracyl)-ethoxy]-iminomethylcamptothecin, 7-(4-pyridyl)-methoxyiminomethyl-camptothecin, 7-(2-thienyl)-methoxyiminomethyl-camptothecin, 7-[(N-methyl)-4- piperidinyl]-methoxyiminomethylcamptothecin, 7-[2-(4-morpholininyl]-ethoxy]-iminomethylcamptothecin, 7-(benzoyloxyiminomethyl)-camptothecin, 7-[(1-hydroxyimino)-2-phenylethyl)-camptothecin, 7-ter-butyloxy-iminomethyl-camptothecin N-oxide, 7-methoxyiminomethyl-camptothecin N-oxide, irinotecan and its active metabolite SN-38.

In an even more preferred embodiment, the camptothecin derivative is selected from the group consisting of 7-t-butoxy-iminomethylcamptothecin, 7-benzyloxyiminomethylcamptothecin, 7-(2-amino)-ethoxyiminomethyl-camptothecin, irinotecan and its active metabolite SN-38.

In another preferred embodiment, within said combination the chemotherapeutic agent (b) is a PARP-1 inhibitor.

In a more preferred embodiment, the PARP-1 inhibitor is chosen from the group consisting of AZD2281, ABT 888 and MK-4827.

In another further preferred embodiment, within said combination the chemotherapeutic agent (b) is an intercalating DNA agent chosen between doxorubicin, dactinomycin and daunorubicin.

In another further preferred embodiment, within said combination the chemotherapeutic agent (b) is an alkylating agent chosen from the group consisting of cisplatin, carboplatin, nedaplatin, oxaliplatin and satraplatin.

A more preferred embodiment consists of the use of a pharmaceutical agent (a) comprising at least one artemisinin-based compound selected from the group consisting of ART, DHA and ARM in combination with a chemotherapeutic agent (b) selected from the group consisting of camptothecin derivatives, PARP-1 inhibitors, intercalating DNA agents and alkylating agents, wherein such use is separate, concomitant or sequential, as a medicament.

A further preferred embodiment consists of the use of a pharmaceutical agent (a) comprising at least one artemisinin-based compound selected from the group consisting of ART, DHA and ARM in combination with a chemotherapeutic agent (b) selected from the group consisting of camptothecin derivatives, PARP-1 inhibitors, intercalating DNA agents and alkylating agents; wherein such use is separate, concomitant or sequential, for the prevention and/or treatment of neoplasms.

Another more preferred embodiment consists of the use of a pharmaceutical agent (a) which is DHA in combination with a pharmaceutical agent (b) which is 7-(2-amino)-ethoxyiminomethylcamptothecin, 7-t-butoxyiminomethyl-camptothecin, irinotecan or its active metabolite SN-38, wherein such use is separate, concomitant or sequential, for the prevention and/or treatment of neoplasms.

A further more preferred embodiment consists of the use of a pharmaceutical agent (a) which is DHA in combination with a pharmaceutical agent (b) which is doxorubicin, wherein such use is separate, concomitant or sequential, for the prevention and/or treatment of neoplasms.

An even more preferred embodiment consists of the use of a pharmaceutical agent (a) comprising at least one artemisinin-based compound selected from the group consisting of ART, DHA and ARM in combination with a chemotherapeutic agent (b) selected from the group consisting of PARP-1 inhibitors, wherein such use is separate, concomitant or sequential, for the prevention and/or treatment of neoplasms.

A still further preferred embodiment consists of the use of a pharmaceutical agent (a) comprising at least one artemisinin-based compound selected from the group consisting of ART, DHA and ARM in combination with a pharmaceutical agent (b) which is an alkylating agent, wherein such use is separate, concomitant or sequential, for the prevention and/or treatment of neoplasms.

A more preferred embodiment consists of the use of a pharmaceutical agent (a) which is DHA in combination with a pharmaceutical agent (b) which is cisplatin or carboplatin, wherein such use is separate, concomitant or sequential, for the prevention and/or treatment of neoplasms.

The expressions "separate use" or "use separately" indicate that each agent (a) and (b) can follow a proper administration schedule which can be different from the one of the other agent.

The expressions "concomitant use" or "use concomitantly" indicate that each agent are administered at the same time, said agents being formulated in one single dosage from or separately, whatever their specific dosages are.

The expressions "sequential use" or "use sequentially" indicate that each agent dosage schedule is administered on a periodic basis, involving only one agent, (a) or (b) at any one time.

The term "neoplasm" indicates an abnormal mass of tissue as a result of neoplasia. Neoplasia consists of the abnormal proliferation of cells. The growth of this clone of cells exceeds, and is uncoordinated with that of the normal tissues around it. It usually causes a tumour. Neoplasms may be benign, pre-malignant or malignant. Benign neoplasms include for example uterine fibroids and melanocytic nevi and do not transform into cancer. Potentially malignant neoplasms include carcinoma in situ. They do not invade and destroy the surrounding tissue but, given enough time, will transform into a cancer. Malignant neoplasms are commonly called cancer. They invade and destroy the surrounding tissue, may form metastases and eventually kill the host. Metastasis consists of the spread of a disease from one organ or part to another non-adjacent organ or part. Only malignant tumour cells and infections have the established capacity to metastasize.

Cancer cells can break away, leak, or spill from a primary tumour, enter lymphatic and blood vessels, circulate through the bloodstream, and be deposited within normal tissues elsewhere in the body. Metastasis is one of three hallmarks of malignancy. Most tumours can metastasize, although in varying degrees (e.g., glioma and basal cell carcinoma rarely metastasize). When tumour cells metastasize, the new tumour is called a secondary or metastatic tumour, and its cells are like those in the original tumour.

According to an embodiment of the present invention the neoplasm to be treated is a primary tumour, selected from the group comprising sarcoma, carcinoma, melanoma, bone tumour, neuroendocrine tumour, lymphoid leukaemia, myeloid leukaemia, monocytic leukaemia, megakaryocytic leukaemia, acute promyelocytic leukaemia or Hodgkin's disease.

The above mentioned sarcoma and carcinoma consist of the group comprising: breast cancer; lung cancer, including non-small cell lung cancer (NSCLC) and small-cell lung cancer (SCLC); gastrointestinal cancer, including esophageal, gastric, small bowel, large bowel, rectal and colon cancer; glioma, including glioblastoma; ovarian cancer, cervical cancer, endometrial cancer, mesothelioma; renal cancer; prostate cancer and skin cancers.

The neoplasm can also refer to a paediatric cancer. For example paediatric cancers that can be treated or where the progression of the condition can be delayed according to the present invention are selected from the group consisting of: acute lymphoblastic leukaemia, acute myeloid leukaemia, adrenocortical carcinoma, astrocytomas, bladder cancer, brain stem glioma, central nervous system atypical teratoid/rhabdoid cancer, brain cancer, central nervous system embryonal cancers, brain cancer, astrocytomas, craniopharyngioma, ependymoblastoma, ependymoma, childhood medulloblastoma, medulloepithelioma, pineal parenchymal cancers of intermediate differentiation, supratentorial primitive neuroectodermal cancers and pineoblastoma, breast cancer, bronchial cancers, carcinoid cancer, cervical cancer, chordoma, colorectal cancer, oesophageal cancer, extra cranial germ cell cancer, gastric cancer, glioma, hepatocellular (liver) cancer, Hodgkin lymphoma, kidney cancer, laryngeal cancer, leukaemia, acute lymphoblastic/myeloid leukaemia, liver cancer, non-Hodgkin lymphoma, medulloblastoma, mesothelioma, multiple endocrine neoplasia syndrome, nasopharyngeal cancer, oral cancer, ovarian cancer, pancreatic cancer, papillomatosis, renal cell cancer, rhabdomyosarcoma, salivary gland cancer, sarcoma, skin cancer, thymoma and thymic carcinoma, thyroid cancer and vaginal cancer.

The expression "prevention of neoplasms" relates to the use of the combination of the present invention to prevent the development of malignant tumours whenever pre-malignant (also called potentially malignant) neoplasm are detected.

According to a further embodiment of the present invention the neoplasm to be treated is a malignant neoplasm, also called cancer, or a potentially malignant neoplasm.

A further embodiment of the present invention is related to the use of a chemotherapeutic combination consisting of a pharmaceutical agent (a) comprising at least one artemisinin-based compound selected from the group consisting of ART, DHA and ARM in combination with a chemotherapeutic agent (b) selected from the group consisting of camptothecin derivatives, PARP-1 inhibitors, intercalating DNA agents and alkylating agents, for the preparation of a medicament useful for the prevention and/or treatment of neoplasms wherein the antitumoural activity is derived from the cytotoxic, and/or apoptotic properties of the chemotherapeutic composition.

A still further embodiment of the present invention is related to the use of said chemotherapeutic composition wherein the tumour is selected from the group comprising sarcoma, carcinoma, melanoma, bone tumour, neuroendocrine tumour, lymphoid leukaemia, myeloid leukaemia, monocytic leukaemia, megakaryocytic leukaemia, acute promyelocytic leukaemia or Hodgkin's disease.

A still further embodiment consists of a pharmaceutical composition comprising a pharmaceutical agent (a) selected from the group consisting of ART, DHA and ARM; and a chemotherapeutic agent (b) selected from the group consisting of camptothecin derivatives, PARP-1 inhibitors, intercalating DNA agents and alkylating agents; which further comprises a pharmaceutically acceptable carrier and/or excipient and/or diluent.

A further object of the invention is a process for the preparation of a pharmaceutical composition as above defined characterised by mixing a pharmaceutical agent (a) as above defined and at least one chemotherapeutic agent (b) as above defined with at least one suitable pharmaceutically acceptable carrier and/or excipient and/or diluent.

In a further preferred embodiment, the agents (a) and (b) can be administered together or one after the other in one combined unit dosage form or in two separate unit dosage forms respectively.

In an even further preferred embodiment, chemotherapeutic agent (b) is administered straight after administration of pharmaceutical agent (a).

Another even further preferred embodiment of the present invention relates to a commercial package or product comprising a pharmaceutical formulation of a pharmaceutical agent (a); and a pharmaceutical formulation of a chemotherapeutic agent (b) for separate, concomitant or sequential use.

A still further preferred embodiment of the present invention relates to a commercial package or product wherein pharmaceutical agent (a) is formulated together with chemotherapeutic agent (b).

In an even most preferred embodiment of the present invention, the agents (a) and (b) demonstrate additive or even preferably synergistic effects.

Another embodiment of the present invention relates to a method for the prevention and/or treatment of neoplasms which comprises treating the patient concurrently or sequentially with a combination of at least one artemisinin-based compound (a) selected from the group consisting of ART, DHA and ARM and at least one chemotherapeutic agent (b) selected from the group consisting of camptothecin derivatives, PARP-1 inhibitors, intercalating DNA agents and alkylating agents.

The term "pharmaceutical agent(s)" or "compound", as used herein, is meant to include the single agents (a) and (b), their pharmaceutically acceptable salts and, according to the context, can also be referred to the combination of the two.

The term "unit dosage form" refers to physically discrete units suitable as unitary dosages for human subjects and other mammals, each unit containing a predetermined quantity of active ingredient (a) or (b) calculated to produce the desired therapeutic effect when administered concomitantly or sequentially, in association with a suitable pharmaceutical excipient. Typical unit dosage forms include refilled, pre-measured ampoules or syringes of the liquid compositions; or pills, tablets, capsules or the like in the case of solid compositions. In such compositions, the compound (a) and compound (b) of the invention are usually a minor component (from about 0.1 to about 50% by weight or preferably from about 1 to about 40% by weight) with the remainder being various vehicles or carriers and processing aids helpful for forming the desired dosing form. Dosage treatment may be a single dose schedule or a multiple dose schedule.

The term "combined unit dosage form" refers to physically discrete units suitable as unitary dosages for human subjects and other mammals, each unit containing a predetermined quantity of active ingredient (a) and (b) calculated to produce the desired therapeutic effect, in association with a suitable pharmaceutical excipients.

As above disclosed, the combination of active ingredients (a) and (b) of the present invention is useful as a medicament for the treatment of cancer diseases where the cancer disease is a cancer of the breasts, pancreas, lung, pleura, peritoneum, face and neck, bladder, brain, prostate, ovaries, eyes or a metastatic cancer.

The term "commercial package" or "product", as used herein, defines a kit of parts allowing separate appropriate dosages of pharmaceutical agents (a) and (b) for concurrent or subsequent use.

The compositions covered by the present invention are entirely conventional and are obtained with methods which are common practice in the pharmaceutical industry, such as, for example, those illustrated in Remington's Pharmaceutical Science Handbook, Mack Pub. N.Y.—last edition. According to the administration route chosen, the compositions will be in solid or liquid form, suitable for oral, parenteral or topical administration. The compositions according to the present invention contain, along with the active ingredients, at least one pharmaceutically acceptable vehicle or excipient. These may be particularly useful formulation coadjuvants, e.g. solubilising agents, dispersing agents, suspension agents, and emulsifying agents.

The amount of the pharmaceutical agents actually administered will typically be determined by a physician, in the light of the relevant circumstances, including the condition to be treated, the chosen route of administration, the actual compounds administered, drug combination, the age, body weight, and response of the individual patient, the severity of the patient's symptoms, and the like. For any compound, the therapeutically effective dose can be estimated initially either in cell culture assays or in animal models, usually mice, rats, guinea pigs, rabbits, dogs, or pigs. The animal model may also be used to determine the appropriate concentration range and route of administration. Such information can then be used to determine useful doses and routes for administration in humans. In calculating the Human Equivalent Dose (HED) it is recommended to use the conversion table provided in Guidance for Industry and Reviewers document (2002, U.S. Food and Drug Administration, Rockville, Md., USA).

Generally, an effective dose will be from 0.01 mg/kg to 2000 mg/kg of pharmaceutical agents, preferably from 0.05 mg/kg to 500 mg/kg of pharmaceutical agent. The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal or rectal means.

The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The medicament may also contain a pharmaceutically acceptable carrier, for administration of a therapeutic agent. Such carriers include antibodies and other polypeptides, genes and other therapeutic agents such as liposomes, provided that the carrier does not induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol.

Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

The term "therapeutically effective dose" refers specifically to the cumulative dose of the combination involving pharmaceutical agent (a) and (b).

A further object of the invention is a process for the preparation of pharmaceutical compositions characterised by mixing at least one pharmaceutical agent (a) and a pharmaceutical agent (b) with suitable excipients, stabilizers and/or pharmaceutically acceptable diluents.

BIOLOGICAL EXPERIMENTS

Example 1

Anti-Proliferative Activity of DHA and ART on Different Tumour Cells

The biological activity of DHA and ART on tumour cells survival was evaluated. The latter were seeded in 96-well tissue culture plates at approximately 10% confluence and were allowed to attach and recover for at least 24 h before being exposed to DHA or ART for 24 h at 37° C. They were then washed to remove DHA and ART and left to recover for 48 hours in medium culture. The medium culture was then removed and cells were washed three times with PBS. The plates were then incubated for on ice for 1 hour with 200 µl of PBS and 50 µl of cold 80% TCA before being washed with distilled water, dried on paper and finally at 40° C. for 5 minutes. 200 µl of 0.4% sulphorodamine B in 1% acetic acid were added and the incubation was prolonged for 30 minutes. Sulphorodamine B was removed, and the plates were washed 3 times with 1% acetic acid. They were finally dried on paper followed by standing at 40° C. for 5 minutes. Then 200 µl Tris 10 mM were added, the plates were kept under stirring for 20 minutes. Cell survival was determined as optical density at 540 nm by means of a Multiskan spectrofluorimeter. The amount of cells killed was expressed as the percentage decrease in sulphorodamine B binding compared to control cultures. IC50 were generated with their standard deviations by the ALLFIT program.

Results

ART showed a very weak antiproliferative effect on tumour cells. With the exception of the NSCLC line (i.e., NCI-H460), DHA showed to be able to inhibit non-resistant tumour cell lines in sub-micromolar range or even at lower concentrations. DHA was indeed, unexpectedly equally effective on the resistant breast tumour cell line MCF-7/Dx MDR and on the non-resistant one (MCF-7). The same analysis could be elaborated with regard to the colon carcinoma cell lines (i.e., LoVo). The resistant LoVo/Dx MDR cell line proved to be 63 times less sensitive to doxorubicin than its non resistant cell line counterpart. Interestingly, the resistant cell lines showed to be not resistant to DHA (resistant index values inferior to 1). Detailed results are shown in table 1 underneath.

TABLE 1

|  | IC50 ± SD (µM) | |
| --- | --- | --- |
| Tumour cell lines | ART | DHA |
| HCT116 | 257 ± 28.8 | 0.37 ± 0.08 |
| SW620 | ND | 1.8 ± 0.1 |
| HT29 | ND | 5.8 ± 0.5 |
| LoVo | >200 | 2.57 ± 0.8 |
| LoVo/Dx MDR | >200 | 1.18 ± 0.3 (0.46) |
| MCF-7 | 45.8 ± 11.5 | 1.05 ± 0.08 |
| MCF-7/Dx MDR | 187 ± 70 (4) | 0.97 ± 0.3 (0.92) |

TABLE 1-continued

| Tumour cell lines | IC50 ± SD (μM) | |
|---|---|---|
| | ART | DHA |
| A2780 | ND | 0.23 ± 0.02 |
| NCI-H460 | ND | 8.16 ± 0.5 |

ND: Not determined,
in brackets, are reported the resistance index values calculated.

Example 2

Synergistic Interaction Between DHA and Various Chemotherapeutic Drugs on Tumour Cells Tumour cells were grown in RPMI 1640 containing 10% foetal bovine serum and treated as described in example 1 with the exception that instead of being exposed only to ART or DHA, the cell lines were treated with the drugs reported in table 2 in combination with DHA (from 1.0 μM to 20 μM, table 2). Tumour cells were treated for 2 h with DHA prior to exposure to further chemotherapeutic agents for 72 h. Cell survival was then evaluated through sulphorodamine B test. Data gathered from the various combination experiments were analyzed using Calcusyn software (Biosoft, Ferguson, Mo.) through the elaboration of isobolograms to determine if the combinations of DHA and the various chemotherapeutic agents were additive, synergistic or antagonistic. Viability assay results (SRB) were expressed as the fraction of cells killed when exposed to a single drug or to a drug combination with respect to the untreated cells. A combination index value (CI) was determined by means of the Chou-Talalay median effect method (T-C Chou, et al., Trends Pharmacol. Sci., 1983, 4, 450), wherein synergism can be defined when CI<1 and the lower the CI parameter value, the stronger the synergism (as defined by CalcuSyn 2.0 analyzer).

Results

As shown in the table 2, good to very good synergistic interactions were found between DHA and different chemotherapeutic agents (PARP-1 inhibitors, camptothecin derivatives, anthracyclines and platinum compounds) on several tumour cell lines of various hystotypes (i.e., non-small cell lung carcinoma, ovarian, colon, breast, epidermoid skin, pancreas carcinoma and glioblastoma).

Depending on the cell type, particularly interesting synergistic combinations were found.

TABLE 2

| | | | Combination index values | | |
|---|---|---|---|---|---|
| Entry | Drugs | Cell lines | $ED_{50}$ | $ED_{75}$ | $ED_{90}$ |
| 1 | Cisplatin | NCI-H460 | 0.79 | 0.88 | 0.98 |
| 2 | Phenanthridinone | NCI-H460 | 0.19 | 0.20 | 0.22 |
| 3 | | A2780 | 0.003 | 0.05 | 0.67 |
| 4 | AZD2281 | NCI-H460 | 0.62 | 0.48 | 0.42 |
| 5 | | HCT116 | 0.36 | 0.34 | 0.31 |
| 6 | | SW620 | 0.60 | 0.55 | 0.66 |
| 7 | | A431 | 0.37 | 0.02 | 0.02 |
| 8 | | A2780/DDP | 0.63 | 0.68 | 0.63 |
| 9 | | CAPAN-1 | 0.35 | 0.49 | 0.73 |
| 10 | | MDA-MB436 | 0.28 | 0.30 | 0.68 |
| 11 | ABT-888 | NCI-H460 | 0.78 | 0.61 | 0.49 |
| 12 | | HCT116 | 0.66 | 0.66 | 0.66 |
| 13 | | A431 | 0.45 | 0.49 | 0.37 |
| 14 | | MDA-MB436 | 0.42 | 0.43 | 0.47 |
| 15 | | CAPAN-1 | 0.59 | 0.32 | 0.22 |
| 16 | MK-4827 | NCI-H460 | 0.83 | 0.83 | 0.84 |
| 17 | SN-38 | NCI-H460 | 0.81 | 0.68 | 0.59 |
| 18 | Doxorubicin | NCI-H460 | 0.76 | 0.53 | 0.37 |
| 19 | Carboplatin | NCI-H460 | 0.53 | 0.71 | 0.95 |
| 20 | Cisplatin | NCI-H460 | 0.79 | 0.88 | 0.98 |
| 21 | 7-(2-amino)-ethoxyiminomethyl-camptothecin | NCI-H460 | 0.39 | 0.24 | 0.16 |
| 22 | Temozolomide | U87MG | 0.24 | 0.35 | 0.72 |
| 23 | | Capan-1 | 0.52 | 0.58 | 0.66 |
| 24 | | MDA-MB436 | 0.75 | 0.79 | 0.89 |

Example 3

In Vivo Antitumor Activity of the Combination Involving DHA and the PARP-1 Inhibitor (AZD2281)

NCI-H460 non-small cell lung carcinoma cells were inoculated subcutaneously (s.c.) in the right flank of CD1 nude mice ($3 \times 10^6$/0.1 ml of Medium 199). Treatments started three days after tumour injection. Mice were subdivided (10 mice/group) in the following experimental groups:
a) Vehicle (DMSO 10%) 10 ml/kg, i.p.;
b) DHA 200 mg/kg, p.o. qdx5/wx3w;
c) AZD2281 100 mg/kg, i.p. qdx5/wx3w;
d) AZD2281+DHA (doses and schedules as above).

For the latter experiment DHA was administered immediately before AZD2281.

To evaluate the antitumour activity, tumour diameters were measured with a Vernier calliper according to the formula $$TV = d^2 \times D/2$$

where d and D are the shortest and longest diameters, respectively.

When tumours reached a volume of about 1500 mm$^3$, mice were sacrificed by cervical dislocation. The efficacy of the drug was assessed as the tumour volume inhibition according to the formula reported underneath:

$$TVI\ \% = 100 - \left[\left(\frac{\text{mean } TV \text{ of treated group}}{\text{mean } TV \text{ of control group}}\right) \times 100\right]$$

Body weight recording was carried out to evaluate body weight loss as calculated in the equation underneath:

$$\%\ BWL = 100 - \left[\frac{BW_{day_x}}{BW_{day_1}}\right] \times 100$$

Wherein BW day x corresponds to the mean weight at day x of the experiment meanwhile BW day 1 corresponds to the mean weight at the first day of the experiment.

Results

Both compounds (i.e., DHA and AZD2281) were well-tolerated since mice did not show any body weight loss during the treatment. When DHA was given orally at 200 mg/kg according to the schedule qdx5/wx3w prior to administration of AZD2281 (i.p. at 100 mg/kg) according to the same schedule, the combination produced a substantial tumour growth inhibition of 31% against NCI-H460 non-small cell lung carcinoma xenografted, meanwhile no antitumor effect was seen when the molecules were given singularly. (Table 3).

TABLE 3

| Drugs | Dose (mg/10 ml/kg) | BWL % | TV ± SE | TVI % |
|---|---|---|---|---|
| Vehicle | — | 0 | 1615 ± 266 | — |
| DHA | 200 p.o. | 0 | 1575 ± 191 | 3 |
| AZD2281 | 100 i.p. | 1 | 1603 ± 171 | 1 |
| DHA + AZD2281 | 200 p.o. + 100 i.p. | 0 | *1120 ± 135 | 31 |

*P < 0.05 versus vehicle treated group (Mann-Whitney).

Example 4

In Vivo Antitumour Activity of the Combination Involving DHA and the PARP-1 Inhibitors AZD2281 and ABT-888

HCT116 colon cancer cells were inoculated subcutaneously (s.c.) in the right flank of CD1 nude mice ($5 \times 10^6$/0.1 ml of Medium 199). Treatments started three days after tumour injection. Mice were subdivided (8 mice/group) in the following experimental groups:
a) Vehicle (DMSO 10%) 10 ml/kg, i.p.;
b) DHA 200 mg/kg, p.o. qdx5/wx4w;
c) AZD2281 100 mg/kg, i.p. qdx5/wx4w;
d) AZD2281+DHA (doses and schedules as above);
e) ABT-888 50 mg/kg, i.p. qdx5/wx4w;
f) ABT-888+DHA (doses and schedules as above).

DHA was administered immediately before AZD2281 or ABT-888.

The antitumour activity was evaluated according to the protocol reported hereinabove in example 3 when tumours reached a volume of about 500 mm$^3$.

Body weight recording was carried out to evaluate body weight loss according to the protocol reported hereinabove in example 3.

Results

All compounds (i.e., DHA, AZD2281 and ABT-888) were well-tolerated since mice did not show any body weight loss during the treatment. None of them when given singularly did show any antitumor effect on this tumour hystotype. When DHA was given orally at 200 mg/kg according to the schedule qdx5/wx4w prior to administration of AZD2281 (i.p. at 100 mg/kg) according to the same schedule, the combination gave rise to a substantial tumour growth inhibition of 37%. Such a synergistic effect was found to be even more pronounced when DHA was combined with another PARP-1 inhibitor, ABT-888 (p.o. at 50 mg/kg) showing a tumour volume inhibition of 49%. (Table 4).

TABLE 4

| Drugs | Dose (mg/10 ml/kg) | BWL % | TV ± SE | TVI % |
|---|---|---|---|---|
| Vehicle | — | 0 | 401 ± 22 | — |
| DHA | 200 p.o. | 1 | 447 ± 39 | 0 |
| AZD2281 | 100 i.p. | 1 | 328 ± 52 | 18 |
| DHA + AZD2281 | 200 p.o. + 100 i.p. | 3 | *252 ± 46 | 37 |
| ABT-888 | 50 i.p. | 0 | 395 ± 56 | 2 |
| DHA + ABT-888 | 200 p.o. + 50 i.p. | 0 | **205 ± 45 | 49 |

*P < 0.05 and
**P < 0.01 versus vehicle treated group (Mann-Whitney).

The invention claimed is:

1. A synergistic chemotherapeutic combination consisting of: (a) dihydroartemisinin (DHA) and (b) a PARP-1 inhibitor, wherein (a) and (b) are formulated separately from each other or are formulated in a single dosage form and wherein the PARP-1 inhibitor is ABT-888.

2. The synergistic chemotherapeutic combination as defined in claim 1 wherein the DHA and PARP-1 inhibitor are formulated in a single dosage form.

3. The synergistic chemotherapeutic combination as defined in claim 1 wherein the DHA and PARP-1 inhibitor are formulated separately.

4. A medicament comprising the synergistic chemotherapeutic combination of claim 1.

5. A pharmaceutical composition comprising the synergistic chemotherapeutic combination as defined in claim 1 and at least one pharmaceutically acceptable carrier and/or excipient and/or diluent.

6. The synergistic chemotherapeutic combination of claim 1, wherein the synergistic chemotherapeutic effect is observed against a human cancer cell line selected from the group consisting of non-small cell lung carcinoma, ovarian, colon, breast, epidermoid skin, pancreatic carcinoma and glioblastoma.

* * * * *